United States Patent
Sekiguchi et al.

(10) Patent No.: US 11,492,655 B2
(45) Date of Patent: Nov. 8, 2022

(54) METHOD OF DETECTING A NUCLEIC ACID

(71) Applicant: Toray Industries, Inc., Chuo (JP)

(72) Inventors: Shota Sekiguchi, Kamakura (JP); Mai Nakagawa, Kamakura (JP); Masateru Ito, Kamakura (JP); Shinjiro Sawada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 484 days.

(21) Appl. No.: 16/345,040

(22) PCT Filed: Nov. 10, 2017

(86) PCT No.: PCT/JP2017/040505
§ 371 (c)(1),
(2) Date: Apr. 25, 2019

(87) PCT Pub. No.: WO2018/088502
PCT Pub. Date: May 17, 2018

(65) Prior Publication Data
US 2019/0276876 A1    Sep. 12, 2019

(30) Foreign Application Priority Data
Nov. 10, 2016 (JP) .............................. JP2016-219465

(51) Int. Cl.
*C12Q 1/68* (2018.01)
*C12Q 1/6806* (2018.01)

(52) U.S. Cl.
CPC ............ *C12Q 1/6806* (2013.01); *C12Q 1/68* (2013.01)

(58) Field of Classification Search
None
See application file for complete search history.

(56) References Cited

U.S. PATENT DOCUMENTS

| 5,234,809 | A | 8/1993 | Boom | |
|---|---|---|---|---|
| 2002/0104801 | A1 | 8/2002 | Voute | |
| 2006/0166190 | A1* | 7/2006 | Xie | C12Q 1/6844 435/5 |
| 2006/0177836 | A1* | 8/2006 | McKernan | C12Q 1/6869 435/6.16 |
| 2012/0003710 | A1* | 1/2012 | Leinweber | C12Q 1/6806 977/773 |
| 2019/0085317 | A1 | 3/2019 | Sekiguchi | |

FOREIGN PATENT DOCUMENTS

| JP | 2002-510787 | 4/2002 |
|---|---|---|
| JP | 2007-006728 A | 1/2007 |
| WO | 2006/107686 | 10/2006 |
| WO | 2017/159763 A1 | 9/2017 |

OTHER PUBLICATIONS

Kim et al. Ultrafast colorimetric detection of nucleic acids based on the inhibition of the oxidase activity of cerium oxide nanoparticles. Chem. Commun.; 2014; 50; 9577-9580. (Year: 2014).*
Kim et al. Ultrafast colorimetric detection of nucleic acids based on the inhibition of the oxidase activity of cerium oxide nanoparticles. Chem. Commun.; 2014; 50; 9577-9580 (Supplemental information) (Year: 2014).*
Martin et al. DNA mismatch repairand the transition to hormone independence in breast and prostate cancer. Cancer Letters; 2010; 291:142-149. (Year: 2010).*
Martin et al. Cancer Letters; 2010; 291:142-149. (Year: 2010).*
Pignatelli et al. Journal of Clinical Laboratory Analysis; 1995; 9:138-140. (Year: 1995).*
Kim et al. Chem. Commun.; 2014; 50; 9577-9580. (Year: 2014).*
Paulier, R., et al., "Attaching DNA to Nanoceria: Regulating Oxidase Activity and Fluorescence Quenching." *ACS Applied Materials & Interfaces*, 5 (15):6820-6825, Aug. 14, 2013. http://dx.doi.org/10.1021/am4018863. Abstract Only.
Agrawal, P., et al., "Solution structure of the major G-quadruplex formed in the human VEGF promoter in $K^+$: insights into loop interactions of the parallel G-quadruplexes." *Nucleic Acids Research*, 41(22):10584-10592, 2013. https://www.ncbi.nlm.nih.gov/pmc/articles/PMC3905851/.

* cited by examiner

*Primary Examiner* — Jeanine A Goldberg
*Assistant Examiner* — Wahwah T Johnson
(74) *Attorney, Agent, or Firm* — DLA Piper LLP (US)

(57) ABSTRACT

A method of detecting a nucleic acid including a) mixing a solution containing a carboxylic acid and/or a salt thereof, a cerium oxide support and a sample containing a nucleic acid to adsorb said nucleic acid to said cerium oxide support, b) separating said cerium oxide support on which said nucleic acid was adsorbed from the mixture obtained in a), c) collecting said nucleic acid by adding an eluent to said cerium oxide support on which said nucleic acid was adsorbed and separated in b), and d) detecting said nucleic acid collected in c) by a hybridization reaction or a nucleic acid amplification reaction.

6 Claims, No Drawings
Specification includes a Sequence Listing.

METHOD OF DETECTING A NUCLEIC ACID

TECHNICAL FIELD

This disclosure relates to a method of detecting a nucleic acid.

BACKGROUND

The development of experimental techniques using nucleic acids has allowed for a search and analysis for new genes, and the relationship between nucleotide sequence information and the functions have been elucidated. As a result, screening tests and clinical tests by nucleic acid detection have been performed in the medical field as well, for example, identification of a disease such as cancer and identification of exogenous pathogen infections. In recent years, various methods of detecting nucleic acids have been studied, and the sensitivity of detection of nucleic acids has been improved. However, further improvement of the sensitivity of detection of a nucleic acid is required for more advanced gene analysis.

One example of methods of detecting nucleic acids is a method of detecting a target sequence using a microarray, PCR or the like. In such a method of detecting a nucleic acid, it is known that the detection sensitivity is improved by optimizing probes and primers or optimizing reaction conditions. At the same time, it is also known that the purity and the amount of the nucleic acid to be detected may change the sensitivity. In other words, many steps from collection to detection of a nucleic acid affect the results of analysis of genes.

Representative examples of methods of collecting a nucleic acid include phenol-chloroform extraction, ethanol precipitation and nucleic acid adsorption on silica. Among them, the most common method is the Boom method, as described in U.S. Pat. No. 5,234,809 B, in which nucleic acids are adsorbed on a metal oxide containing silica, then eluted, and collected. That method is characterized by the concentration of the nucleic acids along with the collection of the nucleic acids from the nucleic acid-adsorbed silica by a centrifugation operation. However, such a method requires a complicated operation or the use of an organic solvent. Since nucleic acid detection is also utilized in the medical field, a method of collecting and efficiently detecting a nucleic acid without any complicated operation or the use of an organic solvent is preferred.

JP 2007-006728 A describes, as a method of collecting and detecting a nucleic acid without use of any organic solvent, a method of collecting a nucleic acid by adsorbing the nucleic acid using a magnetic inorganic component such as iron oxide as a support. That method has a drawback in that the inorganic component is eluted into a collecting solution for a nucleic acid, thereby reducing the purity of collected nucleic acid. Therefore, a method of coating a polymer or a metal oxide such as a silica, titania and ceria on the inorganic component support is described as well. It is explained that the nucleic acid obtained by this method can be directly used for an enzymatic reaction such as PCR.

Furthermore, there is a method, as another method without an organic solvent, in which a silica gel ion exchange column is used. JP 2002-510787 A describes a method of improving a nucleic acid collection quantity by allowing a silica gel support to be used for an ion exchange column to contain a particle with a high specific gravity such as titania, ceria, zirconia and hafnia to increase the column density.

However, J P 2002-510787 A does not describe the degree of sensitivity of the detection of the nucleic acid.

As described above, methods of collecting a nucleic acid and subsequent detection methods have been studied. However, J P 2007-006728 A does not describe what aspect of the nucleic acid can be collected in practice. The degree of sensitivity of the detection of the nucleic acid is not described, either. Therefore, the conditions described in JP 2007-006728 A were reproduced as precisely as possible in Comparative Example 1 described later, and the sensitivity of detection of a nucleic acid was evaluated by a PCR method. However, according to the method of JP 2007-006728 A, almost no nucleic acid was detected by PCR.

The Applicant hereby incorporates by reference the sequence listing contained in the ASCII text file titled TOR-19-1148_Sequence_Listing.txt, created Apr. 25, 2019 and having 1.91 KB of data.

SUMMARY

We focused on a method of collecting a nucleic acid using a cerium oxide as a support to improve the sensitivity of detection of the nucleic acid. By collecting a nucleic acid under conditions in which a cerium oxide is used as a support and a carboxylic acid is contained, the sensitivity of detection of the collected nucleic acid, particularly nucleic acid having a higher order structure can be improved.

We thus provide:

(1) A method of detecting a nucleic acid, comprising the following steps of:
a) mixing a solution containing a carboxylic acid and/or a salt thereof, a cerium oxide support and a sample containing a nucleic acid to adsorb the nucleic acid to the cerium oxide support,
b) separating the cerium oxide support on which the nucleic acid was adsorbed from the mixture obtained in the step a),
c) collecting the nucleic acid by adding an eluent to the cerium oxide support on which the nucleic acid was adsorbed and which was separated in the step b), and
d) detecting the nucleic acid collected in the step c) by a hybridization reaction or a nucleic acid amplification reaction.

(2) A method of detecting a nucleic acid having a higher order structure, comprising the following steps of:
a) mixing a solution containing a carboxylic acid and/or a salt thereof, a cerium oxide support and a sample containing a nucleic acid having a higher order structure to adsorb the nucleic acid to the cerium oxide support,
b) separating the cerium oxide support on which the nucleic acid was adsorbed from the mixture obtained in the step a),
c) collecting the nucleic acid by adding an eluent to the cerium oxide support on which the nucleic acid was adsorbed and which was separated in the step b), and
d) detecting the nucleic acid collected in the step c) by a hybridization reaction or a nucleic acid amplification reaction.

(3) The method of detecting a nucleic acid according to (2), wherein the nucleic acid having a higher order structure has any of the following structures: a higher order structure having a base pair formation other than a base pair formation of A and T (U) pairing and G and C pairing as a basic structure, a higher order structure having a non-formation of A and T (U) base paring and G and C base paring as a basic structure, and a higher order structure formed as a result of distortion in the double helix structure having a base pair formation of A and T (U), and G and C as a basic structure.

(4) The method of detecting a nucleic acid according to (2) or (3), wherein the nucleic acid having a higher order structure has any of the followings structures: mismatch structure, bulge structure, loop structure, hairpin structure, dangling end structure, pseudoknot structure, branch structure, quadruplex structure, octaplex structure, triplex structure, and circular structure.

(5) The method of detecting a nucleic acid according to any one of (1) to (4), wherein the carboxylic acid is acetic acid, oxalic acid, citric acid, or ethylenediaminetetraacetic acid (EDTA).

(6) The method of detecting a nucleic acid according to any one of (1) to (5), wherein the eluent is a buffer solution.

It is possible to improve the detection sensitivity in a method of detecting a nucleic acid contained in a sample such as a biological sample, particularly a nucleic acid having a higher order structure, the method comprising a detection step by a hybridization reaction or a nucleic acid amplification reaction.

DETAILED DESCRIPTION

From a fragment of about several tens of bases to a nucleic acid of about several tens of thousands bp in length, particularly a nucleic acid having a higher order structure can be collected and detected with high sensitivity.

The nucleic acid may be dissolved in a solvent and used as a solution of nucleic acid. The solvent used to dissolve the nucleic acid and the solution used for dilution are not particularly limited, but a solution widely used as a solution containing a nucleic acid such as water or a Tris-HCl buffer solution is preferably used.

Examples of nucleic acids include RNA, DNA, RNA/DNA (chimera) and artificial nucleic acids. As examples of DNAs, nucleic acids such as cDNA, cfDNA, mtDNA, microDNA, genomic DNA, and synthetic DNA can be used. Examples of RNAs include total RNA, mRNA, tRNA, rRNA, miRNA, siRNA, snoRNA, snRNA or non-coding RNA, precursors thereof or synthetic RNA. Synthetic DNA and synthetic RNA can be prepared artificially based on a predetermined nucleotide sequence (it may be either natural sequence or non-natural sequence) using, for example, an automated nucleic acid synthesizer.

A nucleic acid can be collected and detected from any sample containing nucleic acids. For any sample containing nucleic acids, a sample containing artificially synthesized nucleic acids may be used, or a sample containing nucleic acids derived from river, sea, soil and the like. Or environmental DNA may be used, or a biological sample may be used. Examples of biological samples that can be used include cell-derived samples such as cultured cells, culture liquids of cultured cells, tissue samples and specimens; samples derived from microorganisms such as bacteria and viruses; samples derived from animals including human such as body fluids and feces; and solutions containing a compound, which has a biological function such as a protein, sugar, lipid in addition to a nucleic acid. When the biological sample is a liquid sample such as a body fluid, our methods may be applied directly after the sample is collected, or a solution may be added after the sample is collected to dilute the liquid sample. When the biological sample is a solid sample such as a cell pellet or tissue fragment, the solid sample may be diluted with water or a buffer solution after being collected and then used our method.

When a biological sample is used, the biological sample may be subjected to a treatment as explained below. The treatment is carried out because the nucleic acid is often capsuled in a compound such as a cell membrane, a cell wall, a vesicle, a liposome, a micelle, a ribosome, a histone, a nuclear membrane, a mitochondrion, a virus capsid, an envelope, an endosome, and an exosome and because they often interact with each other. A treatment to release a nucleic acid from such compounds may be carried out to collect a nucleic acid with a better yield.

For example, the following treatment may be performed to improve the collection efficiency of a nucleic acid from a biological sample containing $E.$ $coli$. A mixture solution of 0.2 M sodium hydroxide and 1% SDS may be added to the biological sample containing $E.$ $coli$ (alkaline denaturation method), or a 10% sarcosyl solution may be added to the biological sample containing $E.$ $coli$ (non-denaturation method by sarcosyl). Lysozyme may be added to these solutions. The sample may also be treated with proteinase K at 37° C. for one hour. Other methods also include a sonication.

The following treatment may be performed on the biological sample to improve the collection efficiency of a nucleic acid from a yeast-containing biological sample. For example, the biological sample can be treated with Zymolyase commercially available from SEIKAGAKU CORPORATION, followed by adding 10% SDS.

The biological sample can be subjected to the following treatment to improve the collection efficiency of a nuclei acid from a cell-containing biological sample. For example, 1% SDS can be added. As another method, 4 M or more of guanidinium chloride, guanidine thiocyanate salt, urea or the like can be added. Sarcosyl may be added to this solution to a concentration of 0.5% or more. Mercaptoethanol may also be added to result in a concentration of 50 mM or more.

In the above operations, an inhibitor of a degradative enzyme for a nucleic acid may be added to suppress degradation of the nucleic acid contained in the biological sample. As an inhibitor of DNase, EDTA may be added in a concentration of 1 mM or less. As an inhibitor of RNase, commercially available RNasin Plus Ribonuclease Inhibitor (Promega Corporation), Ribonuclease Inhibitor (TAKARA BIO INC.), RNase inhibitor (TOYOBO CO., LTD.) and the like can be used.

When DNA and RNA are present together in a biological sample, they can be separated by phenol-chloroform extraction if desired. For example, when phenol-chloroform extraction is performed under acidic conditions, RNA and DNA are separated into an aqueous layer and a chloroform layer, respectively. Under neutral conditions, RNA and DNA are distributed into an aqueous phase. This nature can be utilized to select the conditions depending on the type of the desired nucleic acid. The above-mentioned chloroform may be replaced by p-bromoanisole.

In the phenol-chloroform extraction, a commercially available reagent, ISOGEN (registered trademark: NIPPON GENE CO., LTD.), TRIzol (registered trademark: Life Technologies Japan Ltd.), RNAiso (TAKARA BIO INC.), or 3D-Gene (registered trademark: Toray Industries, Inc.) RNA extraction reagent from liquid sample kit (Toray Industries, Inc.) may be used. A single step in the treatments described above may be performed alone, or in combination with another step of a different operation. The concentration of the solution to be used may vary as appropriate.

A nucleic acid, particularly a nucleic acid having a higher order structure can be detected with high sensitivity.

The higher order structure of a nucleic acid is generally classified into a higher order structure formed due to a nucleotide sequence of a nucleic acid and a higher order structure formed by a complex of a nucleic acid and a protein. A nucleic acid having either higher order structure can be preferably used, but a nucleic acid having a higher order structure formed due to a nucleotide sequence of a nucleic acid can be more preferably used.

The higher order structure formed due to a nucleotide sequence of a nucleic acid is, in the formation of base pairing, classified into a structure having a basic structure of a base pair formation other than a base pair formation of A and T (U) pairing and G and C pairing, a structure having a basic structure of a non-formation of A and T (U) base paring and G and C base paring, and a structure formed as a result of distortion in the double helix structure having a base pair formation of A and T (U), and G and C. A nucleic acid having any structure can be preferably used.

Examples of the higher order structure having a basic structure of a base pair formation other than a base pair formation of A and T (U) pairing and G and C pairing include mismatch structures including a single nucleotide polymorphism (SNP) (terminal mismatch structure, G and T mismatch structure, G and A mismatch structure, G and G mismatch structure, tandem mismatch structure). For example, the mismatch structure is contained in miRNA, tRNA, mRNA, rRNA, precursors of miRNA, genomic RNA, genomic DNA, and cell free DNA.

Examples of the higher order structure having a basic structure of a non-formation of A and T (U) base paring and G and C base paring include bulge structures, hairpin structures, loop structures, dangling end structures, pseudoknot structures, branch structures, quadruplex structures (guanine quadruplex, i-Motif).

The bulge structure is a structure in which there is no base to bind in a base pair forming sequence chain and thus a base pair is not formed. For example, the bulge structure is contained in miRNA, tRNA, mRNA, rRNA, precursors of miRNA, genomic RNA, genomic DNA, cell free DNA and the like.

The hairpin structure is a structure in which a nucleotide sequence consisting of single-stranded RNA, DNA or the like is arranged around an axis of one point in a symmetric and complementary way, and these RNA and DNA are linked between complementary bases. For example, the hairpin structure is contained in miRNA, tRNA, mRNA, rRNA, precursors of miRNA, genomic RNA, genomic DNA, cell free DNA and the like.

The loop structure is a structure in which a part of the nucleotide sequence of RNA and DNA in the above hairpin structure is not complementary and that part unwinds without forming a base pair. For example, the loop structure is contained in miRNA, tRNA, mRNA, rRNA, precursors of miRNA, genomic RNA, genomic DNA, cell free DNA and the like. The dangling end structure is a structure in which either one of the 3' end and the 5' end protrudes with base pairing formed. For example, the dangling end structure is contained in miRNA, tRNA, mRNA, rRNA, precursors of miRNA, genomic RNA, genomic DNA, cell free DNA and the like.

The pseudoknot structure is a loop structure in which two or more of the above loop structures are repeated via the base pairing part. For example, the pseudoknot structure is contained in viral genomic DNA, viral genomic RNA, ribozymes and the like.

The branch structure is a structure in which one or a plurality of nucleic acid chains partially occur in the branched chain part where the above higher order structure is formed. For example, the branch structure is contained in mRNA, rRNA and the like.

The quadruplex structure (guanine quadruplex, i-Motif) and the octaplex structure is a structure formed from one or more chains having a nucleic acid sequence in which one of G and C bases is present in abundance partially at one or more positions. For example, the quadruplex structure (guanine quadruplex, i-Motif) is contained in genomic DNA, and is contained in a causative gene which causes polyglutamine diseases and repeat diseases among others and a telomere region.

Examples of the higher order structure formed as a result of distortion in the double helix structure having a basic structure of base pair formation of A and T (U), and G and C include triplex structures, circular structures (closed circular structures, open circular structures, supercoils) and the like. For example, circular structures are included in mitochondrial DNA, plasmids, circular genomes possessed by microorganisms such as *E. coli* or yeast, viral genomes such as HPV and the like.

Examples of the higher order structure formed by a complex of a nucleic acid and a protein include higher order structures of a modifier (DNA methyltransferase, RNA methyltransferase, T4 polynucleotide kinase, histone, etc.), a transcription factor (such as those classified as RNA polymerase), a replication factor (such as those classified as DNA polymerase), a reverse transcription factor (reverse transcriptase), a transposable element (transposase), a translational factor (such as constituent units of a ribosome), cleavage enzymes (such as restriction enzymes) a signal transfer factor, a factor involved in an immune response and the like. A higher order structure of a nucleic acid having any of these proteins can be preferably used as a nucleic acid having a higher order structure.

The nucleic acid having a higher order structure explained above may be a naturally occurring nucleic acid, an artificially synthesized nucleic acid, or a nucleic acid synthesized by genetic engineering. A methylated or phosphorylated nucleic acid may also be used.

The carboxylic acid refers to an organic acid having at least one carboxyl group. Examples of the carboxylic acid having one carboxyl group include acetic acid, formic acid, propionic acid, butyric acid, valeric acid, caproic acid, enanthic acid, caprylic acid, pelargonic acid, capric acid, lauric acid, myristic acid, palmitic acid, margaric acid, stearic acid, oleic acid, linoleic acid, linolenic acid, arachidonic acid, eicosapentaenoic acid, docosahexaenoic acid, sorbic acid, benzoic acid, salicylic acid, gallic acid, cinnamic acid, lactic acid and the like. Examples of the carboxylic acid having two carboxyl groups include oxalic acid, malonic acid, succinic acid, glutaric acid, adipic acid, fumaric acid, maleic acid, phthalic acid, isophthalic acid, terephthalic acid, malic acid, pimelic acid, suberic acid, azelaic acid, tartronic acid, tartaric acid, citraconic acid, mesaconic acid, itaconic acid, cyclopropanedicarboxylic acid, cyclobutanedicarboxylic acid, cyclopentanedicarboxylic acid, cyclohexanedicarboxylic acid, iminodiacetic acid, a-ketoglutaric acid, glutamic acid, aspartic acid, N-(2-hydroxyethyl)iminodiacetic acid and the like. Examples of the carboxylic acid having three carboxyl groups include aconitic acid, citric acid, isocitric acid, propane-1,2,3-tricarboxylic acid, butane-1,2,3,4-tetracarboxylic acid, triethyl-1,1,2-ethanetricarboxylic acid, cyclobutanetricarboxylic acid, cyclohexanetricarboxylic acid, hemimellitic acid, trimellitic acid, trimesic acid, nitrilotriacetic acid and the like. Examples of the carboxylic acid having four carboxyl groups include cyclohexanetetracarboxylic acid, merophanic acid, prenitic acid, pyromellitic acid, ethylenediaminetetraacetic acid (EDTA), (18-crown-6)-2,3,11,12-tetracarboxylic acid, trans-1,2-diaminocyclohexane-N,N,N',N'-tetraacetic acid, and O,O'-bis(2-aminoethyl)ethylene glycol-N,N,N',N'-tetra acetic acid. Examples of the carboxylic acid having five or more carboxyl groups include benzene pentacarboxylic acid, diethylenetriaminepentaacetic acid, diethylenetriamine-N,N,N',N'',N'''-pentaacetic acid, cyclohexanehexacarboxylic acid, mellitic acid, a hexacarboxylic acid of dierythritol, triethylenetetramine-N,N,N',N'',N''',N''''-hexaacetic acid, cyclooctanedicarboxylic acid, octaacetic acid of triethylrythol and the like. Among these, preferred carboxylic acids are acetic acid, oxalic acid, citric acid, or ethylenediaminetetraacetic acid (EDTA).

As the carboxylic acid, salts of the above-mentioned carboxylic acids may be used. As a salt of a carboxylic acid, a Li salt, a Na salt, a K salt, a Rb salt, a Cs salt and the like can be used. Specific examples of salts of acetic acid include Li salts, Na salts, K salts, Rb salts, Cs salts and the like. Examples of salts of oxalic acid include Li salts, 2Li salts, Na salts, 2Na salts, K salts, 2K salts, Rb salts, 2Rb salts, Cs salts, 2Cs salts and the like. Examples of salts of citric acid include Li salts, 2Li salts, 3Li salts, Na salts, 2Na salts, 3Na salts, K salts, 2K salts, 3K salts, Rb salts, 2Rb salts, 3Rb salts, Cs salts, 2Cs salts, 3Cs salts and the like. Examples of salts of EDTA include Li salts, 2Li salts, 3Li salts, 4Li salts, Na salts, 2Na salts, 3Na salts, 4Na salts, K salts, 2K salts, 3K salts, 4K salts, Rb salts, 2Rb salts, 3Rb salts, 4Rb salts, Cs salts, 2Cs salts, 3Cs salts, 4Cs salts and the like. Organic salts having an amine such as ammonium salts, ethylamine salts, diethylamine salts, triethylamine salts, ethanolamine salts and the like are also included. Among these salts, sodium acetate, potassium acetate, disodium oxalate, dipotassium oxalate, sodium citrate, disodium citrate, trisodium citrate, potassium citrate, dipotassium citrate, tripotassium citrate, disodium EDTA, trisodium EDTA, EDTA tetrasodium, dipotassium EDTA, tripotassium EDTA, and tetrapotassium EDTA are preferred.

A carboxylic acid and a salt of a carboxylic acid may be used in combination, or a mixture of different types of carboxylic acids and carboxylic acid salts may be used.

The hybridization reaction refers to a reaction in which a nucleic acid to be detected and a probe form a pair with each other via a hydrogen bond. Hybridization reactions can occur intermolecularly or intramolecularly in nucleic acids having mutually complementary nucleotide sequences or sequences having high homology to the complementary nucleotide sequences.

The probe used in the hybridization reaction refers to a nucleic acid molecule having a nucleotide sequence complementary to the nucleotide sequence of DNA or RNA to be detected or a nucleotide sequence highly homologous to the complementary sequence. The nucleotide sequence of the nucleic acid to be detected may be a sense strand, an antisense strand or both. When the hybridization reaction is carried out, only one probe may be used, or a plurality of probes may be used. For a specific detection, the length of the probe is preferably 16 bases or more. As the nucleic acid molecule, DNA, RNA, a modified nucleic acid, LNA, BNA, PNA, a morpholino nucleic acid, a photoresponsive nucleic acid, nucleotide and the like can be used. Among these nucleic acid molecules, only one kind may be used or a plurality of kinds may be used. The nucleic acid molecule at the end of the probe may be modified with a fluorescent dye or a chemical functional group, and a base of the nucleic acid molecule may be deleted.

As the hybridization reaction, for example, a method of mixing a solution containing a nucleic acid and a solution containing a probe and carrying out a hybridization reaction can be used to detect the nucleic acid, or a method of immobilizing either a nucleic acid or a probe on a substrate such as a solid, gel or the like and carrying out a hybridization reaction can be used to detect the nucleic acid. Specific examples of such methods include microarray methods, Northern blotting methods, Southern blotting methods, sandwich hybridization, slot blot hybridization, plaque hybridization, colony hybridization, in situ hybridization, FISH methods and the like.

The amplification reaction of the nucleic acid is a reaction in which a specific sequence is selectively amplified using a polymerase and a nucleic acid as a template. Specifically, a PCR method, a LCR method, a LAMP method or the like can be used. The PCR method may further include a real-time PCR, RT-PCR, competitive PCR, anchored PCR, TaqMan PCR, random PCR, multiplex PCR, shuttle PCR, PCR/GC-clamp method, stretch PCR, Alu PCR, megaprimer PCR, Immuno-PCR, AP-PCR, SHARP method, consensus PCR, RNA-primed PCR, LA-PCR, RACE method, Hot Start PCR, inverse PCR, recombination PCR, degenerate PCR, cycling probe PCR, quantitative PCR, SDA method, colony PCR, DNA sequencing, in situ PCR, single cell PCR, PCR of environmental DNA, sequencing of environmental DNA, DNA barcoding, DNA shuffling, and the like, and any PCR method can be preferably used.

The sensitivity of detection of a nucleic acid in the step of detecting a nucleic acid can be evaluated by determining the efficiency of the hybridization reaction or the PCR efficiency.

The efficiency of the hybridization reaction can be evaluated by the electrophoresis, the Tm measurement or the like. The efficiency of the hybridization reaction is preferably evaluated by electrophoresis when the base length of each of the sequence to be detected and the probe is sufficiently short, and by the Tm measurement when the base length of each of the sequence to be detected and the probe is sufficiently long.

The efficiency of the hybridization reaction can be evaluated by electrophoresis as follows. First, 3 solutions of a nucleic acid having the sequence to be detected are prepared at the same concentration. The first one is used directly for electrophoresis. One or more equivalents of the probe used for detection are added to the second one, which is then left still for about 1 hour or more before the electrophoresis. For the third one, using our method, the same equivalent of the probe as in the second sample is added to the nucleic acid collected in the step (c), and the solution is left still for the same period of time as in the second sample before the electrophoresis. By electrophoresis, in addition to the band detected in the first sample, in the second and third samples, a new band is confirmed by the hybridization of the probe with the sequence to be detected. A part of the gel where any band is not seen is taken as the background in a software such as image analysis, and the difference between this value and the intensity of the band is taken as the signal intensity of the band. The signal intensity ratio of the bands is calculated as the ratio of the third sample to the second sample, and if the value is larger than 1, it can be evaluated that the efficiency of the hybridization reaction has improved.

The efficiency of the hybridization reaction can be evaluated by the Tm measurement as follows. In the Tm measurement, the variation in absorbance at 260 nm accompanying the process of the dissociation of the double stranded nucleic acid to single strands by raising the temperature is measured. The melting curve in which the temperature is plotted on the horizontal axis and the absorbance is plotted on the vertical axis is traced. An inflection point is observed in the melting curve, which is the temperature at which 50% of the nucleic acid double strands melt (Tm). In this measurement, it is necessary to measure in advance the theoretical value of the Tm of the probe or the measured value of the Tm of the probe.

In the Tm measurement method, 4 solutions of a nucleic acid having the sequence to be detected are prepared at the same concentration. The first one is used directly for the Tm measurement. One or more equivalents of the probe used for detection are added to the second one, which is then left still for about 1 hour or more before the Tm measurement. For the third one, using our method, the nucleic acid collected in the step (c) is used in the Tm measurement. The fourth one is subjected to the adsorption and elution treatment on a cerium oxide support, and the same equivalent of the probe as in the second sample is added to the eluent, and the solution is left still for the same period of time as in the second sample before the Tm measurement. Subsequently, in determining the efficiency of the hybridization reaction, a melting curve is used. The absorbance at the Tm of the probe is determined for all samples from the melting curve. The difference between the second sample and the first sample and the difference between the fourth sample and the third sample are taken individually, and the ratio of the latter with the former taken as 1 is calculated to obtain the efficiency of the hybridization reaction. When the value larger than 1 is obtained, it can be evaluated that the efficiency of the hybridization reaction has improved. The efficiency of a hybridization reaction may be high when this ratio is 1.1 or more, preferably 1.2 or more, more preferably 1.3 or more. For the Tm measurement, a device in which an ultraviolet-visible absorptiometer and a temperature control unit are connected can be used.

The efficiency of PCR can be determined by the real-time PCR as follows. For the efficiency of PCR in the real-time PCR, 2 solutions of a nucleic acid having the sequence to be detected are prepared at the same concentration. A forward primer and a reverse primer are directly added to the first one as a probe. For the second one, using our method, the same equivalent of the forward primer and the reverse primer as in the first sample is added to the nucleic acid collected in the step (c), followed by the real-time PCR.

In the real-time PCR method, an amplification curve in which the number of cycles is plotted on the horizontal axis and the fluorescence intensity is plotted on the vertical axis can be obtained. In this amplification curve, the number of cycles when a certain signal intensity is reached (Cq value, Ct value) is obtained. The difference between the Cq value of the first sample and the Cq value of the second sample is taken. From this difference, a value as an exponent of the power (power exponent) of base 2 is calculated and considered as the PCR efficiency. It can be evaluated that the PCR efficiency has improved when this value is 1.4 or more. This value is more preferably 1.6 or more, still more preferably 1.8 or more.

Cerium oxide is an amphoteric oxide having $CeO_2$ as a basic structure, also called ceria, and has no solubility in water. For the cerium oxide, naturally-produced cerium oxide or cerium oxide manufactured industrially may be used. Examples of the methods of producing cerium oxide include a method in which oxalate or carbonate salt is pyrolytically decomposed, a method in which a hydroxide precipitate obtained by neutralizing a solution of nitrate salt or the like is calcined (neutralization method), and a vapor phase method. Cerium oxide manufactured industrially can be available from reagent manufacturers, catalyst chemical manufacturers, Japan Reference Catalyst of Catalysis Society of Japan and the like.

For the cerium oxide support, a granulated one is suitable. The particle size may be uniform, or those with different particle sizes may be combined in use in the support. For the particle size, for example, cerium oxide particles of 100 μm or less, preferably 50 μm or less, more preferably 10 μm or less, can be used.

A 50% diameter (D50, a median diameter) determined by a frequency distribution of the sphere equivalent diameter measured by the measurement using a particle size analyzer based on laser diffraction scattering method is used.

For the eluent, water or a buffer solution can be used, and a buffer solution is preferred.

As a buffer solution, a phosphate buffer solution containing phosphoric acid and sodium phosphate, a citrate buffer solution containing citric acid and sodium citrate, a Tris-EDTA buffer solution obtained by adding EDTA to a Tris-hydrochloric acid buffer solution containing tris(hydroxymethyl)aminomethane and hydrochloric acid or the like can be preferably used. Among these, a citrate buffer solution containing citric acid and sodium citrate and a Tris-EDTA buffer solution obtained by adding EDTA to a Tris-hydrochloric acid buffer solution containing tris(hydroxymethyl)aminomethane and hydrochloric acid are particularly preferred because these buffer solutions have a chelating activity. The pH of the buffer solution is preferably pH 4 or more and pH 9 or less, more preferably pH 5 or more and pH 8 or less.

A chelating agent may be added to the buffer solution to impart a chelating activity to the buffer solution. A chelating agent is a substance that has a ligand with a plurality of coordination positions and binds to a metal ion to form a complex. A buffer solution containing a chelating agent has a chelating activity.

Specific examples of chelating agents added to a buffer solution include ethylenediaminetetraacetic acid (EDTA), nitrilotriacetic acid (NTA), glycol ether diamine tetraacetic acid (EGTA), polyphosphoric acid, metaphosphoric acid and/or salts thereof. The final concentration of the chelating agent is preferably 50 mM or more, and is more preferably 100 mM or more, and further preferably 500 mM or more.

Examples of compounds as a chelating agent other than the above include anionic polymers. Since a polymer which has carboxylic acid on the side chains coordinate to a metal ion, the buffer solution may contain such a polymer. Examples of polymers having such a function include polyvinyl sulfonic acid and/or salt thereof. The final concentration is not particularly limited as long as it is 1 wt % or more, and preferably 10 wt % or more. Our method of detecting a nucleic acid, especially a nucleic acid having a higher order structure, comprises:

a) mixing a solution containing a carboxylic acid, a cerium oxide support and a sample containing a nucleic acid to adsorb the nucleic acid to the cerium oxide support, b) separating the support on which the nucleic acid was adsorbed from the solution mixed in a), and c) collecting the nucleic acid by adding an eluent to the support on which the nucleic acid was adsorbed and separated in b), d) detecting the nucleic acid collected in c) by a hybridization reaction or a nucleic acid amplification reaction.

Each step will be described in detail below.

Step a) is a step of mixing a solution containing a carboxylic acid and/or a salt thereof, a cerium oxide support and a sample containing a nucleic acid to adsorb the nucleic acid to the cerium oxide support. A sample containing a carboxylic acid and a nucleic acid may be mixed in advance and then mixed with a cerium oxide support, or a carboxylic acid and a cerium oxide support may be mixed in advance and then mixed with a sample containing a nucleic acid. As a stage before the nucleic acid is adsorbed, the cerium oxide support may be washed in advance with a solution such as water or ethanol to remove impurities adsorbed on the surface, or this washing operation may be omitted.

The concentration of the carboxylic acid is not particularly limited, but when a carboxylic acid having 1 or 2 carboxyl groups is used, the final concentration of the mixture mixed in step a) may be 0.01 mM or more and 100 mM or less, and when a carboxylic acid having 3 or more carboxyl groups is used, the final concentration may be 0.01 mM or more and 1 mM or less. The method of mixing the cerium oxide support with the sample containing a nucleic acid is not particularly limited, but may be carried out, for example, by pipetting or mixing by inversion, or using an instrument such as a mixer or vortex. The mixing time is not particularly limited, but may be about 1 minutes, or may be a longer time. The support may be packed in a column and a sample containing the nucleic acid may be allowed to pass through the column.

In step a), a compound other than the carboxylic acid or a salt of the carboxylic acid may be added to a solution containing the carboxylic acid and/or a salt thereof. For example, protein denaturants such as guanidine thiocyanate salts and guanidine hydrochloride salts, salts such as sodium chloride and lithium chloride, and reducing agents such as mercaptoethanol, which are all widely used in the collection of nucleic acids, can be added.

Step b) is a step of separating the cerium oxide support on which the nucleic acid was adsorbed from the mixture obtained in step a). Examples of separation methods include a method in which the mixture obtained in step a) is centrifuged so that the cerium oxide support on which the nucleic acid is adsorbed is allowed to precipitate, and the supernatant is then removed. Since the specific gravity of the cerium oxide support on which the nucleic acid is adsorbed is higher than that of water, the support can be easily allowed to precipitate by the centrifugation operation. Conditions for centrifugation may be, for example, preferably a treatment at 6000 G or more and 20000 G or less for 1 minute, and more preferably a treatment at 10000 G or more and 20000 G or less for 1 minute. Other separation methods include a method in which an ultrafiltration membrane is used. The mixture obtained in step a) is allowed to pass through an ultrafiltration membrane with a smaller pore size than the particle size of the cerium oxide support on which the nucleic acid is adsorbed, and the cerium oxide support on which the nucleic acid is adsorbed is then separated. Such an ultrafiltration membrane is available as a kit, and a centrifugal filter kit as typified by Ultrafree (registered trademark) manufactured by Merck Ltd., or Nanosep (registered trademark) manufactured by Pall Corporation can be obtained for use.

After the operation of step b), the treatment as described below may be carried out if necessary. This is because a biological sample-derived material other than the nucleic acid of interest may be adsorbed on the surface of the cerium oxide support after step a). For example, washing or degradation treatment can be performed to isolate the nucleic acid in higher purity. Specifically, various treatments, can be performed such as washing with water to remove non-specifically adsorbed compounds; washing with a surfactant to remove non-specifically adsorbed proteins; washing with a surfactant-containing solution to remove ions and low-molecular compounds; washing with an organic solvent to remove non-specifically adsorbed hydrophobic compounds; adding a protease to degrade non-specifically adsorbed proteins; adding a ribonuclease to isolate only DNA, and adding an DNA nuclease to isolate only RNA.

Step c) is a step of collecting the nucleic acid by adding an eluent to the cerium oxide support on which the nucleic acid was adsorbed which support was separated in step b). Step c) is a step of collecting the nucleic acid by adding an eluent to the cerium oxide support on which the nucleic acid was adsorbed and eluting the adsorbed nucleic acid into the eluent.

With respect to collecting the nucleic acid by adding the above eluent, examples of a method of separating the cerium oxide support and the solution of the eluted nucleic acid include a method of, in step c), centrifuging a mixture obtained by adding the eluent to the support on which the nucleic acid was adsorbed to precipitate the support, and obtaining the supernatant in which the nucleic acid was eluted. Since the specific gravity of the support is greater than that of water, the support can be easily allowed to precipitate by the centrifugation operation. Conditions for centrifugation may be, for example, preferably a treatment at 6000 G or more and 20000 G or less for 1 minute, and more preferably a treatment at 10000 G or more and 20000 G or less for 1 minute.

Other methods of separating the cerium oxide support and the solution of the eluted nucleic acid include a method in which an ultrafiltration membrane is used. The mixture obtained in step c) is allowed to pass through an ultrafiltration membrane with a smaller pore size than the particle size of the cerium oxide support, which results in separating the cerium oxide support. Such an ultrafiltration membrane is available as a kit, and a centrifugal filter kit as typified by Ultrafree (registered trademark) manufactured by Merck Ltd., or Nanosep (registered trademark) manufactured by Pall Corporation can be obtained for use.

A nucleic acid thus collected can be chemically modified as necessary. Examples of chemical modifications include fluorescent dye modification, quencher modification, biotin modification, amination, carboxylation, maleinimidation, succinimidation, phosphorylation and dephosphorylation, to an end of a nucleic acid, and the other examples include staining by an intercalator or a groove binding agent. These modifications may be introduced by chemical reaction, or may be introduced by enzyme reaction. These modification groups are introduced, and the modification group introduced via chemical modification is quantified instead of quantifying collected nucleic acid itself, whereby the nucleic acid can be also indirectly quantified.

Step d) is a step of detecting the nucleic acid collected in step c) by a hybridization reaction or a nucleic acid amplification reaction. Specifically, at the same time as the hybridization reaction or the amplification reaction of the nucleic acid, or after the hybridization reaction or the amplification reaction of the nucleic acid, a conventional detection means such as enzymatic reaction, electrophoresis, absorbance measurement, fluorescence detection or the like is used to detect the nucleic acid.

In the above hybridization reaction, it is also possible to perform a treatment that promotes the hybridization reaction. Examples thereof include annealing by a heat treatment, adding a metal ion such as magnesium or zinc, forming a covalent bond by light irradiation, adding a chemical crosslinking agent such as formalin to form a covalent bond and the like.

EXAMPLES

Our methods will be more specifically described by the following Examples.

Materials and Methods

Cerium oxide particles used as a support were obtained from DAIICHI KIGENSO KAGAKU KOGYO CO., LTD. and were used directly in the experiments. SYBR Premix Ex Taq II was purchased from TAKARA BIO INC. and SYBR Gold for gel staining was purchased from Invitrogen Corporation. They were used directly without any particular purification. Other reagents were purchased from Wako Pure Chemical Industries, Ltd., Nacalai Tesque Inc., and Sigma-Aldrich Japan, and used directly as purchased without any particular purification.

CUTE MIXER CM-1000 manufactured by TOKYO RIKAKIKAI CO, LTD. was used as a mixer; CFX 96 manufactured by Bio-Rad Laboratories, Inc. was used as PCR; UV 1650 and TMS PC-8 manufactured by Shimadzu Corporation were used for Tm measurement; and WSE-1100 manufactured by ATTO Corporation was used for the acrylamide gel electrophoresis. The stained acrylamide gel was imaged with FLA 9500 manufactured by GE Healthcare Japan Corp., the image was analyzed using ImageQuant TL manufactured by GE Healthcare Japan Corp.

Nucleic acids represented by SEQ ID NOs: 1 to 10 were purchased from Eurofin Genomics Kabushiki Kaisha and used as purchased without any particular purification.

Nucleic acid having a supercoiled structure: "pUC19"

As the nucleic acid having a supercoiled structure, pUC19 was prepared as follows and used. Plasmid DNA (2.7 kbp, pUC19), which is a nucleic acid having a circular structure, was cloned in *E. coli* DH5a (TKR 9057) manufactured by TAKARA BIO INC. and purified with Wizard Plus SV Minipreps DNA Purification System (A 1460) manufactured by Promega Corporation. The purified pUC19 was subjected to electrophoresis on an agarose gel and separated into three fractions of the closed circle, the open circle and the linear structure, and only the fraction having the closed circular structure was isolated using NucleoSpin Gel and PCR Clean-up (740609) manufactured by MACHEREY-NAGEL Corporation, and used as a nucleic acid having a supercoiled structure (hereinafter referred to as "pUC19") in the following experiments.

As a primer to detect the pUC19 by PCR, the nucleic acid represented by SEQ ID NO: 1 (forward primer) and the nucleic acid represented by SEQ ID NO: 2 (reverse primer) were used.

Nucleic Acid Having a Guanine Quadruplex Structure: "G4"

As the nucleic acid having a higher order structure, a nucleic acid having a guanine quadruplex structure was prepared as follows. Based on the sequence information of Pu22-T12T13 in P. Agrawal et. al., Nucl. Acids Res. 2013, 41, 10584-10592, describing a sequence that forms a guanine quadruplex structure nucleic acids represented by the nucleotide sequences of SEQ ID NO: 3 and SEQ ID NO: 4 were designed. In the nucleic acids represented by SEQ ID NO: 3, 23rd to 44th bases from the 5' end are a guanine quadruple structure forming site. The guanine quadruplex structure can be prepared by adding potassium to an already known sequence which forms a guanine quadruplex structure and annealing it. According to Agrawal et al., a guanine quadruplex structure was formed. Briefly, the nucleic acid represented by SEQ ID NO: 3 was dissolved in a buffer solution (pH 7) of 10 mM Tris-HCl, 1 mM EDTA, and 75 mM KCl to achieve the final concentration of 1 µM, and the solution was heated at a heating rate of 0.5° C./min from 20° C. to 95° C., and an annealing operation of cooling to a room temperature was carried out twice, followed by the use in the experiments. The nucleic acid subjected to this treatment is described as "G4".

The probe 1 represented by the nucleotide sequence of SEQ ID NO: 4 was used as a probe for hybridization for G4 detection. The probe 1 is labeled with 5'-Cy5 and is capable of hybridizing with the 1st to 22nd bases from the 5' end of the nucleotide sequence of SEQ ID NO: 3.

Nucleotide Acid Having Partially a Bulge Structure, a Loop Structure, a Hairpin Structure, a Dangling End Structure, a Pseudoknot Structure: "Loop 1"

As the model of the nucleotide acid forming partially a bulge structure, a loop structure, a hairpin structure, a dangling end structure, or a pseudoknot structure, a nucleic acid having the nucleotide sequence represented by SEQ ID NO: 5 was designed. In the nucleotide sequence of SEQ ID NO: 5, the 20th base from the 5' end corresponds to the site forming a bulge structure, a loop structure, a hairpin structure, or a pseudoknot structure, and the 40th to 45th bases from the 5' end correspond to the site forming a dangling end structure. The nucleic acid represented by SEQ ID NO: 5 was dissolved in a buffer solution (pH 7) of 10 mM Tris-HCl and 1 mM EDTA to achieve the final concentration of 1 µM, and the solution was heated at a heating rate of 0.5° C./min from 20° C. to 95° C., and an annealing operation of cooling to a room temperature was carried out twice, followed by the use in the experiments. The nucleic acid subjected to this treatment is described as "Loop 1".

Nucleotide Acid Having Partially a Bulge Structure, a Loop Structure, a Hairpin Structure, a Dangling End Structure, a Pseudoknot Structure "Loop 4"

As the model of the nucleotide acid forming partially a bulge structure, a loop structure, a hairpin structure, a dangling end structure, a pseudoknot structure, a nucleic acid having the nucleotide sequence represented by SEQ ID NO: 6 was designed. In the nucleotide sequence of SEQ ID NO: 6, the 20th to 23rd bases from the 5' end correspond to the site forming a bulge structure, a loop structure, a hairpin structure, or a branch structure, and the 43rd to 48th bases from the 5' end correspond to the dangling end site. The nucleic acid represented by SEQ ID NO: 6 was dissolved in a buffer solution (pH 7) of 10 mM Tris-HCl and 1 mM EDTA to achieve the final concentration of 1 µM, and the solution was heated at a heating rate of 0.5° C./min from 20° C. to 95° C., and an annealing operation of cooling to a room temperature was carried out twice, followed by the use in the experiments. The nucleic acid subjected to this treatment is described as "Loop 4".

Nucleotide Acid Having Partially a Bulge Structure, a Loop Structure, a Hairpin Structure, a Dangling End Structure, a Pseudoknot Structure: "Loop 8"

As the model of the nucleotide acid forming partially a bulge structure, a loop structure, a hairpin structure, a dangling end structure, a pseudoknot structure, a nucleic acid having the nucleotide sequence represented by SEQ ID NO: 7 was designed. In the nucleotide sequence of SEQ ID NO: 7, the 20th to 27th bases from the 5' end correspond to the site forming a bulge structure, a loop structure, a hairpin structure, or a branch structure, and the 47th to 52nd bases from the 5' end correspond to the dangling end site. The nucleic acid represented by SEQ ID NO: 7 was dissolved in a buffer solution (pH 7) of 10 mM Tris-HCl and 1 mM EDTA to achieve the final concentration of 1 µM, and the solution was heated at a heating rate of 0.5° C./min from 20° C. to 95° C., and an annealing operation of cooling to a room temperature was carried out twice, followed by the use in the experiments. The nucleic acid subjected to this treatment is described as "Loop 8".

Nucleic Acid not Having a Higher Order Structure: Nucleic Acids Represented by SEQ ID NOs: 9 and 10

As a nucleic acid not having a higher order structure, nucleic acids which have nucleotide sequences represented by SEQ ID NOs: 9 and 10 and which do not have any structure of a mismatch structure, a bulge structure, a loop structure, a hairpin structure, a dangling end structure, a pseudoknot structure, a branch structure, a quadruplex structure, an octaplex structure or a circular structure were designed. In the nucleic acids represented by SEQ ID NOs: 9 and 10, 1st to 25th bases from the 5' end hybridize with each other. The nucleic acids represented by SEQ ID NOs: 9 and 10 were dissolved in a buffer solution (pH 7) of 10 mM Tris-HCl and 1 mM EDTA to achieve the final concentration of 1 µM, and both of the solutions were mixed in equal amounts for the preparation. The mixture was heated at a heating rate of 0.5° C./min from 20° C. to 95° C., and an annealing operation of cooling to a room temperature was carried out twice. Then, electrophoresis was performed, and it was verified that only one band was observed for the use in the subsequent experiments.

Probes to Detect a Nucleic Acid not Having the Loop 1, Loop 4, Loop 8, or a Higher Order Structure Based on the Loop 1, Loop 4, Loop 8, and the nucleic acids represented by SEQ ID NOs: 9 and 10 as nucleic acids not having a higher order structure, the probe 2 represented by SEQ ID NO: 8 was used as a probe for hybridization to detect the nucleic acids prepared above. The probe 2 is labeled with 5'-Cy5. The probe 2 can hybridize with 21st to 45th bases from the 5' end of the Loop 1 (SEQ ID NO: 5), 24th to 48th bases from the 5' end of the Loop 4 (SEQ ID NO: 6), 28th to 52nd bases from the 5' end of the Loop 8 (SEQ ID NO: 7), and the 1st to 25th bases from the 5' end of SEQ ID NO: 9, respectively.

Comparative Example 1 A Method of Collecting and Detecting pUC19 Under Conditions not Containing Carboxylic Acid and/or Salts of Carboxylic Acid The pUC19, which is a nucleic acid having a higher order structure, was collected under conditions not containing carboxylic acid and/or salts of carboxylic acid, and the PCR efficiency was determined.

A method of collecting a nucleic acid using cerium oxide as a support as described in Examples of JP 2007-006728 A was investigated. In addition, to reproduce the same conditions as those described in JP 2007-006728 A, a nucleic acid adsorption solution was prepared by mixing water and a 10 mM Tris-HCl buffer solution (pH 7) having a buffering action between pH 5 to pH 9, and an eluent was prepared by mixing water and a 0.5 M phosphate buffer solution. The experiments were carried out as follows.

First, cerium oxide particles were weighed in an amount of 2.0 mg in four 1.5-ml tubes. To each tube, 200 µl of ethanol was added, and each resulting mixture was vortex-mixed and then centrifuged for 1 minute by a centrifuge to remove the supernatant. This operation was further repeated twice to wash the cerium oxide particles, and the resulting material was used as a cerium oxide support.

Subsequently, 100 µl of water or 10 mM Tris-HCl (pH 7) in which 100 ng of pUC19 was dissolved was added to the washed cerium oxide support, followed by stirring by a mixer for 5 minutes, and the resulting mixture was centrifuged (10000 G, 1 minute) to remove the supernatant. To the remaining support, 200 µl of water was added, and then vortexed. This operation was further repeated twice. Subsequently, 10 µl of water or a phosphate buffer solution (0.5 M, pH 7) was added and the resulting mixture was stirred by a mixer for 15 minutes. The resulting mixtures were centrifuged by a centrifuge (10000 G, 1 minute) and the supernatant was then collected as a nucleic acid solution.

The PCR efficiency was calculated as follows. The pUC19 of 100 ng/10 ul was first diluted with water 50-fold, and 1 µl of the dilute was taken as a template, to which 1 µl of each of 10 µM forward primer and 10 µM reverse primer was added as a probe. Then, 9.5 µl of water was further added, and finally 12.5 µl of SYBR Premix Ex Taq II was added and mixed to prepare 25 µl of a PCR reaction solution. Likewise, an eluent containing the nucleic acid collected using the above-described cerium oxide support was diluted 50-fold with water to prepare 25 µl of the PCR reaction solution having the same composition. Both were detected by real-time PCR according to the shuttle protocol of 2 steps (step 1: 95° C., 30 sec, step 2: 95° C., 5 sec, 56° C., 30 sec, step 2 was carried out for 40 cycles), and the Cq values were compared. The difference from the Cq value of the first sample not subjected to the collection step of the nucleic acid by the cerium oxide support and the Cq value of the second sample subjected to the collection step of the nucleic acid by the cerium oxide support according to the JP 2007-006728 A was calculated. From this difference, an exponent of the power (power exponent) of base 2 was calculated as the PCR efficiency. The results are shown in Table 1.

These results showed that the PCR efficiency were lower than the results of Examples 1, 4 to 7 in which a PCR reaction was carried out using nucleic acids collected under conditions containing carboxylic acid and/or salts of carboxylic acid, which is described below.

TABLE 1

| Solution for adsorption (Final concentration) | Solution for elution | PCR efficiency [times] | |
|---|---|---|---|
| 10 mM Tris-HCl, 1 mM EDTA (pH 7) | 0.5M Phosphate buffer solution (pH 7) | 9.6 | Example 1 |
| 10 mM Tris-HCl, 0.5 mM EDTA (pH 7) | 0.5M Phosphate buffer solution (pH 7) | 6.8 | Example 1 |
| 10 mM Tris-HCl, 0.2 mM EDTA (pH 7) | 0.5M Phosphate buffer solution (pH 7) | 4.3 | Example 1 |
| 10 mM Tris-HCl, 0.1 mM EDTA (pH 7) | 0.5M Phosphate buffer solution (pH 7) | 3.7 | Example 1 |
| 10 mM Tris-HCl, 0.01 mM EDTA (pH 7) | 0.5M Phosphate buffer solution (pH 7) | 3.7 | Example 1 |
| 10 mM Tris-HCl (pH 7) | 0.5M Phosphate buffer solution (pH 7) | 1.3 | Comparative Example 1 |
| Water | 0.5M Phosphate buffer solution (pH 7) | 1.2 | Comparative Example 1 |
| 10 mM Tris-HCl (pH 7) | Water | Not detectable | Comparative Example 1 |
| Water | Water | Not detectable | Comparative Example 1 |

Example 1 Method of Collecting and Detecting pUC19 Under Conditions Containing Disodium EDTA Salt Using a disodium EDTA salt as a salt of carboxylic acid, pUC19 which is a nucleic acid having a higher order structure was collected and PCR efficiency was determined.

Disodium EDTA was added to a Tris-HCl solution so that the final concentration would be 10 mM Tris-HCl (pH 7), and 1 mM, 0.5 mM, 0.2 mM, 0.1 mM, and 0.01 mM EDTA, and 100 ng of pUC19 was dissolved in 100 μl of each solution, and mixed with a cerium oxide support for the adsorption. A 0.5M phosphate buffer solution (pH 7) was used as an eluent. Other conditions and operations were carried out in the same manner as in Comparative Example 1 to calculate the PCR efficiency by the real-time PCR. The results are shown in Table 1.

From these results, we found that the detection of the pUC19 collected using the disodium EDTA salt as a salt of carboxylic acid resulted in the increase in the PCR efficiency by 3.7 times or more, and thus nucleic acids having a supercoiled structure could be detected by PCR with a high sensitivity.

Example 2 Method of Collecting and Detecting pUC19 Under Conditions Containing Disodium EDTA Using disodium EDTA as a salt of carboxylic acid, pUC19 which is a nucleic acid having a higher order structure was collected and the hybridization efficiency was determined.

Disodium EDTA was added to a Tris-HCl solution so that the final concentration would be 10 mM Tris-HCl (pH 7) and 1 mM EDTA, and 500 ng of pUC19 was dissolved in 100 μl of each solution, and mixed with a cerium oxide support for adsorption. As an eluent, 15 μl of a 0.5M phosphate buffer solution (pH 7) was used. The other conditions and operations were carried out in the same manner as in Comparative Example 1 to perform a collection step by a cerium oxide support.

The efficiency of the hybridization reaction was calculated as follows by preparing four samples and measuring their Tm. For the first sample, 7.5 μl (250 ng) of pUC19 adjusted to 500 ng/15 ul was taken, 7.5 μl of a 0.5 M phosphate buffer solution and 4 μl of formamide were added, and then water was added to reach the volume of 100 μl. For the second sample, 5 μl of each of 10 μM forward primer and 10 μM reverse primer was further added as a probe to the first sample, and the sample was completed to 100 μl. For the third sample, a collection operation was performed with the above cerium oxide support, and 7.5 μl of the eluent containing the collected nucleic acid was taken. Then, 4 μl of formamide was added, and the volume was completed to 100 μl with water. For the forth sample, 5 μl of each of 10 μM forward primer and 10 μM reverse primer was further added as a probe to the third sample, and the sample was completed to 100 μl. Each sample was used to measure the Tm and thus a melting curve was obtained. Since the Tm (theoretical value) of the probe used was 60° C., the absorbance at 60° C. was determined for all the samples from the melting curve. The difference between the second sample and the first sample is taken and the difference between the fourth sample and the third sample was taken respectively. The former was taken as 1 and the ratio of the latter was calculated to obtain the efficiency of the hybridization reaction. The results are shown in Table 2.

These results showed that the detection of the collected pUC19 using the EDTA disodium as a salt of carboxylic acid resulted in the improvement of the efficiency of hybridization reaction between the pUC19 and the probe by 1.6 times or more.

TABLE 2

| Solution for adsorption (Final concentration) | Higher order structure | Hybridization efficiency [times] | |
|---|---|---|---|
| 10 mM Tris-HCl, 1 mM EDTA (pH 7) | Supercoil | 1.6 | Example 2 |
| 10 mM Tris-HCl, 1 mM EDTA (pH 7) | Guanine quadruplex | 2.3 | Example 3 |

Example 3 Method of Collecting and Detecting G4 Under Conditions Containing EDTA Using EDTA as carboxylic acid, G4, which is a nucleic acid having a higher order structure, was collected and the hybridization efficiency was determined.

To 10 μl of a solution containing G4, 90 μl of a buffer solution (pH 7) of 10 mM Tris-HCl, 1 mM EDTA, and 75 mM KCl was added, and then mixed with a cerium oxide support for adsorption. For the eluent, a solution obtained by adding 75 mM KCl to 10 μl of 0.5 M phosphate buffer solution (pH 7) was used. The other conditions and operations were carried out in the same manner as in Comparative Example 1 to perform a collection step by a cerium oxide support.

The efficiency of the hybridization reaction was calculated by preparing 3 samples and performing electrophoresis as follows. The first sample is a solution obtained by adding G4 (0.1 μM, 1 μl) after annealing to 1 μl of a loading dye and 4 μl of water. The second sample is a solution obtained by adding a detection probe 1 (0.2 μM, 1 μl) to the G4 (0.1 μM, 1 μl) after annealing, leaving the mixture still for one hour, and then adding 1 μl of a loading dye and 3 μl of water. The third sample is a solution obtained as follows: a collection operation was performed with the above cerium oxide support, and 1 μl of the eluent containing the collected nucleic acid was taken. Then, a detection probe (0.2 μM, 1 μl) was added and left still for one hour, and then 1 μl of a loading dye and 3 μl of water were added. The electrophoresis was carried out on an acrylamide gel at a concentration of 10 wt % for each, followed by double staining with a Cy5 stain modified at the 5' end of the detection probe and SYBR Gold. By electrophoresis, in addition to the band detected in the first sample, a new band was confirmed resulted from hybridization of the detection probe 1 with G4 in the second and third samples. The concentration ratio of this band was calculated as the ratio of the third sample to the second sample by image analysis or the like, and thus the efficiency of the hybridization reaction was determined. The results are shown in Table 2.

These results showed that the detection of the collected G4 using the EDTA as carboxylic acid resulted in the improvement of the efficiency of hybridization reaction with the probe by 2.3 times or more.

Example 4 Method of Collecting and Detecting pUC19 Under Conditions Containing Trisodium Citrate Using trisodium citrate as a salt of carboxylic acid, pUC19 which is a nucleic acid having a higher order structure was collected and PCR efficiency was determined.

Trisodium citrate was added to a Tris-HCl solution so that the final concentration would be 10 mM Tris-HCl (pH 7), and 1 mM, 0.5 mM, 0.2 mM, 0.1 mM, and 0.01 mM trisodium citrate, and 100 ng of pUC19 was dissolved in 100 μl of each solution, and mixed with a cerium oxide support for adsorption. A 0.5M phosphate buffer solution (pH 7) was used as an eluent. Other conditions and operations were carried out in the same manner as in Comparative Example 1 to calculate the PCR efficiency in the real-time PCR. The results are shown in Table 3.

From these results, we found that the detection of the collected pUC19 using the trisodium citrate as a salt of carboxylic acid resulted in the increase in the PCR efficiency by 3.4 times or more, and thus a higher order structure could be detected with by PCR a high sensitivity.

TABLE 3

| Solution for adsorption | PCR efficiency [times] | |
|---|---|---|
| 10 mM Tris, 1 mM Citric acid (pH 7) | 3.5 | Example 4 |
| 10 mM Tris, 0.5 mM Citric acid (pH 7) | 5.4 | Example 4 |
| 10 mM Tris, 0.2 mM Citric acid (pH 7) | 4.6 | Example 4 |
| 10 mM Tris, 0.1 mM Citric acid (pH 7) | 3.5 | Example 4 |
| 10 mM Tris, 0.01 mM Citric acid (pH 7) | 3.4 | Example 4 |

Example 5 Method of Collecting and Detecting pUC19 Under Conditions Containing Disodium Oxalate Using disodium oxalate as a salt of carboxylic acid, pUC19 which is a nucleic acid having a higher order structure was collected and PCR efficiency was determined.

Disodium oxalate was added to a Tris-HCl solution so that the final concentration would be 10 mM Tris-HCl (pH 7), and 50 mM, 20 mM, 1 mM, 0.5 mM, 0.2 mM, 0.1 mM, and 0.01 mM disodium oxalate, and 100 ng of pUC19 was dissolved in 100 μl of each solution, and mixed with a cerium oxide support for adsorption. A 0.5M phosphate buffer solution (pH 7) was used as an eluent. Other conditions and operations were carried out in the same manner as in Comparative Example 1 to calculate the PCR efficiency in the real-time PCR. The results are shown in Table 4.

From these results, we found that the detection of the collected pUC19 using the disodium oxalate as a salt of carboxylic acid resulted in the increase in the PCR efficiency by 2.8 times or more, and thus a higher order structure could be detected with by PCR a high sensitivity.

TABLE 4

| Solution for adsorption | PCR efficiency [times] | |
|---|---|---|
| 10 mM Tris, 50 mM Oxalic acid (pH 7) | 3.6 | Example 5 |
| 10 mM Tris, 20 mM Oxalic acid (pH 7) | 2.8 | Example 5 |
| 10 mM Tris, 1 mM Oxalic acid (pH 7) | 3.5 | Example 5 |
| 10 mM Tris, 0.5 mM Oxalic acid (pH 7) | 5.4 | Example 5 |
| 10 mM Tris, 0.2 mM Oxalic acid (pH 7) | 4.6 | Example 5 |
| 10 mM Tris, 0.1 mM Oxalic acid (pH 7) | 3.5 | Example 5 |
| 10 mM Tris, 0.01 mM Oxalic acid (pH 7) | 3.4 | Example 5 |

Example 6 Method of Collecting and Detecting pUC19 Under Conditions Containing Sodium Acetate Using sodium acetate as a salt of carboxylic acid, pUC19 which is a nucleic acid having a higher order structure was collected and PCR efficiency was determined.

Sodium acetate was added to a Tris-HCl solution so that the final concentration would be 10 mM Tris-HCl (pH 7), and 100 mM, 50 mM, 20 mM, 10 mM, 5 mM, 2 mM, 1 mM, 0.5 mM, 0.2 mM, 0.1 mM, and 0.01 mM sodium acetate, and 100 ng of pUC19 was dissolved in 100 μl of each solution, and mixed with a cerium oxide support for adsorption. A 0.5M phosphate buffer solution (pH 7) was used as an eluent. Other conditions and operations were carried out in the same manner as in Comparative Example 1 to calculate the PCR efficiency in the real-time PCR. The results are shown in Table 5.

From these results, we found that the detection of the collected pUC19 using the sodium acetate as a salt of carboxylic acid resulted in the increase in the PCR efficiency by 3.2 times or more, and thus a nucleic acid having a higher order structure could be detected with by PCR a high sensitivity.

TABLE 5

| Solution for adsorption | PCR efficiency [times] | |
|---|---|---|
| 10 mM Tris, 100 mM Acetic acid (pH 7) | 6.4 | Example 6 |
| 10 mM Tris, 50 mM Acetic acid (pH 7) | 6.7 | Example 6 |
| 10 mM Tris, 20 mM Acetic acid (pH 7) | 5.5 | Example 6 |
| 10 mM Tris, 10 mM Acetic acid (pH 7) | 5.4 | Example 6 |
| 10 mM Tris, 5 mM Acetic acid (pH 7) | 3.5 | Example 6 |
| 10 mM Tris, 2 mM Acetic acid (pH 7) | 3.9 | Example 6 |
| 10 mM Tris, 1 mM Acetic acid (pH 7) | 3.5 | Example 6 |
| 10 mM Tris, 0.5 mM Acetic acid (pH 7) | 3.2 | Example 6 |
| 10 mM Tris, 0.2 mM Acetic acid (pH 7) | 3.9 | Example 6 |
| 10 mM Tris, 0.1 mM Acetic acid (pH 7) | 4.3 | Example 6 |
| 10 mM Tris, 0.01 mM Acetic acid (pH 7) | 4.7 | Example 6 |

Example 7 Method of Collecting and Detecting pUC19 Under Conditions Containing EDTA and an Additive A nucleic acid was collected and detected under the condition in which a protein denaturing agent and reducing agent widely used for nucleic acid detection were added. A guanidine thiocyanate salt and a guanidine hydrochloride salt were used as protein denaturing agents. Sodium chloride, lithium chloride and mercaptoethanol were used as reducing agents. Using EDTA as carboxylic acid, pUC19 which is a nucleic acid having a higher order structure was collected and PCR efficiency was determined.

A guanidine thiocyanate salt, a guanidine hydrochloride salt, sodium chloride, lithium chloride and mercaptoethanol were dissolved in an adsorption solution containing carboxylic acid (10 mM Tris-HCl, 1 mM EDTA (pH 7)) (final concentration: guanidine thiocyanate 6 M, guanidine hydrochloride 6 M, sodium chloride 5 M, lithium chloride 8 M, mercaptoethanol 100 mM, 10 mM, 1 mM), and 100 ng of pUC19 was dissolved in 100 μl of each solution, and mixed with a cerium oxide support for adsorption. A 0.5M phosphate buffer solution (pH 7) was used as an eluent. Other conditions and operations were carried out in the same manner as in Comparative Example 1, to calculate the PCR efficiency in the real-time PCR. The results are shown in Table 6.

From these results, we found the PCR efficiency was 5.8 times or more even when the above additives were added to the solution containing carboxylic acid, and thus a nucleic acid having a higher order structure could be detected with by PCR a high sensitivity.

TABLE 6

| Additive | PCR efficiency [times] | |
| --- | --- | --- |
| 6M Guanidine thiocyanate salt | 6.6 | Example 7 |
| 6MGuanidine hydrochloride salt | 5.8 | Example 7 |
| 5M Sodium chloride | 5.8 | Example 7 |
| 8M Lithium chloride | 5.8 | Example 7 |
| 100 mM Mercaptoethanol | 8.8 | Example 7 |
| 10 mM Mercaptoethanol | 6.3 | Example 7 |
| 1 mM Mercaptoethanol | 6.3 | Example 7 |

Examples 8 to 10 Method of Collecting and Detecting Loop 1, Loop 4, and Loop 8 Under Conditions Containing EDTA Using EDTA as carboxylic acid, Loop 1, Loop 4, and Loop 8 which are nucleic acids having a higher order structure were individually collected and the hybridization efficiency was determined. The result for Loop 1 is Example 8, the result for Loop 4 is Example 9, and the result for Loop 8 is Example 10.

To 3 µl of the solutions containing the Loop 1, the Loop 4, and the Loop 8, respectively, 97 µl of a buffer solution (pH 7) of 10 mM Tris-HCl and 1 mM EDTA was added and mixed with a cerium oxide support for adsorption. As an eluent, 10 µl of a 0.5M phosphate buffer solution (pH 7) was used. Other conditions and operations were carried out in the same manner as in Comparative Example 1 to collect nucleic acids by a cerium oxide support.

The hybridization reaction was carried out in the same manner as in Example 3 except that the Loop 1 (0.3 µM, 1 µl), Loop 4 (0.3 µM, 1 µl), Loop 8 (0.3 µM, 1 µl) and detection probe 2 (1 µM, 1 µl) were used to calculate the hybridization efficiency. The results are shown in Table 7.

These results showed that the detection of the Loop 1, Loop 4, Loop 8 collected using the EDTA as carboxylic acid resulted in the improvement of the efficiency of hybridization reaction by 3.7 times or more for the Loop 1 (Example 8), by 4.7 times or more for the Loop 4 (Example 9), and by 3.8 times or more for the Loop 8 (Example 10).

These results showed that nucleic acids having various higher order structures could be detected with high sensitivity.

TABLE 7

| Solution for adsorption (Final concentration) | Higher order structure | Hybridization efficiency [times] | |
| --- | --- | --- | --- |
| 10 mM Tris-HCl, 1 mM EDTA (pH 7) | Loop 1 SEQ ID NO: 5 | 3.7 | Example 8 |
| 10 mM Tris-HCl, 1 mM EDTA (pH 7) | Loop 4 SEQ ID NO: 6 | 4.7 | Example 9 |
| 10 mM Tris-HCl, 1 mM EDTA (pH 7) | Loop 8 SEQ ID NO: 7 | 3.8 | Example 10 |

Example 11 Method of Collecting and Detecting a Nucleic Acid not Having a Higher Order Structure Under Conditions Containing EDTA Using EDTA as carboxylic acid, nucleic acids represented by SEQ ID NOs: 9 and 10 which are nucleic acids not having a higher order structure were collected and the hybridization efficiency was determined.

To 3 µl of a solution containing nucleic acids represented by SEQ ID NOs: 9 and 10, 97 µl of a buffer solution (pH 7) containing 10 mM Tris-HCl, 1 mM EDTA, and 6M guanidine thiocyanate salt was added, and then mixed with a cerium oxide support for adsorption. As an eluent, 10 µl of a 0.5M phosphate buffer solution (pH 7) was used. Other conditions and operations were carried out in the same manner as in Comparative Example 1 to collect nucleic acids by a cerium oxide support.

The hybridization reaction was carried out in the same manner as in Example 3 except that a nucleic acid not having a higher order structure and the detection probe 2 (1 µM, 1 µl) were used to calculate the hybridization efficiency. The results are shown in Table 8.

These results showed that the detection of the collected nucleic acid using the EDTA as carboxylic acid resulted in the improvement of the efficiency of hybridization reaction by 1.4 times or more even when the nucleic acid not having a higher order structure was used.

TABLE 8

| Solution for adsorption (Final concentration) | Nucleic acid detected | Hybridization efficiency [times] | |
| --- | --- | --- | --- |
| 10 mM Tris-HCl, 1 mM EDTA, 6M Guanidine thiocyanate salt (pH 7) | SEQ ID NO: 9 SEQ ID NO: 10 | 1.4 | Example 11 |

The invention claimed is:

1. A method of detecting a nucleic acid having a higher order structure comprising:
   a) mixing a solution containing a carboxylic acid and/or a salt thereof, a cerium oxide support and a sample containing a nucleic acid having a higher order structure to adsorb said nucleic acid to said cerium oxide support,
   b) separating said cerium oxide support on which said nucleic acid was adsorbed from the mixture obtained in a),
   c) isolating said nucleic acid from cerium oxide support with nucleic acid obtained in b) by adding an eluent,
   d) detecting said nucleic acid isolated in c) by a hybridization reaction or a nucleic acid amplification reaction,
   wherein a concentration of the carboxylic acid is,
      when a carboxylic acid having 1 or 2 carboxyl groups is used, a final concentration of the mixture mixed in step a) is 0.01 mM or more and 100 mM or less, and
      when a carboxylic acid having 3 or more carboxyl groups is used, the final concentration is 0.01 mM or more and 1 mM or less.

2. The method according to claim 1, wherein said nucleic acid having a higher order structure has any of: a higher order structure having a basic structure of a base pair formation other than a base pair formation of A and T (U) pairing and G and C pairing, a higher order structure having a basic structure of a non-formation of A and T (U) base paring and G and C base paring, and a higher order structure formed as a result of distortion in the double helix structure having a basic structure of a base pair formation of A and T (U), and G and C.

3. The method according to claim 1, wherein said nucleic acid having a higher order structure has any of: bulge structure, loop structure, hairpin structure, dangling end structure, pseudoknot structure, branch structure, quadruplex structure, octaplex structure, triplex structure, and circular structure.

4. The method according to claim 2, wherein said nucleic acid having a higher order structure has any of: mismatch structure, bulge structure, loop structure, hairpin structure, dangling end structure, pseudoknot structure, branch structure, quadruplex structure, octaplex structure, triplex structure, and circular structure.

5. The method according to claim 1, wherein said carboxylic acid is acetic acid, oxalic acid, citric acid, or ethylenediaminetetraacetic acid (EDTA).

6. The method according to claim 1, wherein said eluent is a buffer solution.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: artificial
<220> FEATURE:
<223> OTHER INFORMATION: synthesized primer

<400> SEQUENCE: 1
aaggcgatta agttgggtaa                                              20
```

<210> SEQ ID NO 2
<211> LENGTH: 21
<212> TYPE: DNA
<213> ORGANISM: artificial
<220> FEATURE:
<223> OTHER INFORMATION: synthesized primer

<400> SEQUENCE: 2
aacaatttca cacaggaaac a                                              21

<210> SEQ ID NO 3
<211> LENGTH: 44
<212> TYPE: DNA
<213> ORGANISM: artificial
<220> FEATURE:
<223> OTHER INFORMATION: synthesized sequence

<400> SEQUENCE: 3
atatgcgcta tacgcgagct gccggggcgg gccttgggcg ggt                      44

<210> SEQ ID NO 4
<211> LENGTH: 22
<212> TYPE: DNA
<213> ORGANISM: artificial
<220> FEATURE:
<223> OTHER INFORMATION: synthesized probe

<400> SEQUENCE: 4
gcagctcgcg tatagcgcat at                                             22

<210> SEQ ID NO 5
<211> LENGTH: 45
<212> TYPE: DNA
<213> ORGANISM: artificial
<220> FEATURE:
<223> OTHER INFORMATION: synthesized sequence

<400> SEQUENCE: 5
gctatacgcg agctgcgcgt cgcgcagctc gcgtatagcg catat                    45

<210> SEQ ID NO 6
<211> LENGTH: 48
<212> TYPE: DNA
<213> ORGANISM: artificial
<220> FEATURE:
<223> OTHER INFORMATION: synthesized sequence

<400> SEQUENCE: 6
gctatacgcg agctgcgcgc tctcgcgcag ctcgcgtata gcgcatat                 48

<210> SEQ ID NO 7
<211> LENGTH: 52
<212> TYPE: DNA
<213> ORGANISM: artificial
<220> FEATURE:
<223> OTHER INFORMATION: synthesized sequence

<400> SEQUENCE: 7
gctatacgcg agctgcgcgc tctctctcgc gcagctcgcg tatagcgcat at            52

<210> SEQ ID NO 8
<211> LENGTH: 25
<212> TYPE: DNA
<213> ORGANISM: artificial
<220> FEATURE:

```
<223> OTHER INFORMATION: synthesized sequence

<400> SEQUENCE: 8
atatgcgcta tacgcgagct gcgcg                                              25

<210> SEQ ID NO 9
<211> LENGTH: 25
<212> TYPE: DNA
<213> ORGANISM: artificial
<220> FEATURE:
<223> OTHER INFORMATION: synthesized sequence

<400> SEQUENCE: 9
cgcgcagctc gcgtatagcg catat                                              25

<210> SEQ ID NO 10
<211> LENGTH: 25
<212> TYPE: DNA
<213> ORGANISM: artificial
<220> FEATURE:
<223> OTHER INFORMATION: synthesized sequence

<400> SEQUENCE: 10
atatgcgcta tacgcgagct gcgcg                                              25
```